(12) United States Patent
Zhang

(10) Patent No.: US 7,566,551 B2
(45) Date of Patent: Jul. 28, 2009

(54) METHOD OF PRODUCING XANTHOPHYLL

(75) Inventor: Kai Zhang, Iwata (JP)

(73) Assignee: Yamaha Hatsudoki Kabushiki Kaisha, Iwata-shi (JP)

( * ) Notice: Subject to any disclaimer, the term of this patent is extended or adjusted under 35 U.S.C. 154(b) by 44 days.

(21) Appl. No.: 10/578,096

(22) PCT Filed: Apr. 22, 2005

(86) PCT No.: PCT/JP2005/008274
§ 371 (c)(1), (2), (4) Date: Dec. 22, 2006

(87) PCT Pub. No.: WO2005/116238
PCT Pub. Date: Dec. 8, 2005

(65) Prior Publication Data
US 2007/0092932 A1  Apr. 26, 2007

(30) Foreign Application Priority Data
May 26, 2004 (JP) .............................. 2004-156098

(51) Int. Cl.
C12P 23/00 (2006.01)

(52) U.S. Cl. ...................... 435/67; 435/257.1

(58) Field of Classification Search .................. 435/67, 435/257.1; 424/195.17
See application file for complete search history.

(56) References Cited

FOREIGN PATENT DOCUMENTS

| JP | 7-39389 A | 2/1995 |
|---|---|---|
| JP | 2000-60532 A | 2/2000 |
| JP | 2001-61466 A | 3/2001 |
| JP | 2004-129504 A | 4/2004 |

OTHER PUBLICATIONS

Hata et al. Journal of Applied Phycology (2001), 13(5), 395-402.*
Fabregas, "Two-stage cultures for the production of Astaxanthin from *Haematococcus pluvialis*", Journal of Biotechnology, vol. 89, p. 65-71 (2001).
Lorenz, "Commercial potential for *Haematococcus* microalgae as a natural source of astaxanthin", TIBTECH, vol. 18 (April), p. 160-167 (2000).
Tjahjono, "Hyper-accumulation of astaxanthin in a green alga *Haematococcus pluvialis* at elevated temperatures", Biotechnology Letters, vol. 16, No. 2, (February), p. 133-138 (1994).
Furubayashi et al., "Photo-dependent astaxanthin biosynthesis in a green alga, *Haematococcus pluvialis*", Seibutsu Kogakkaishi, 1993, vol. 71, No. 4, pp. 233-237.

* cited by examiner

*Primary Examiner*—Tekchand Saidha
(74) *Attorney, Agent, or Firm*—McLeland Patent Law Office PLLC

(57) ABSTRACT

The present invention provides a method for producing a xanthophyll from a photosynthetic microalga, which includes inoculating a photosynthetic microalga containing a xanthophyll, preferably an encysted microalga, into a nutrient medium to grow the microalga; and encysting the grown microalga, by a single-step culture method in which the growth step and the encystment step are performed continuously using a nutrient medium having a low nitrogen source concentration, or by a two-step culture method in which the microalga is grown in a nutrient medium having a high nitrogen source concentration and then transferred to an encystment medium.

9 Claims, 3 Drawing Sheets

METHOD OF PRODUCING XANTHOPHYLL

TECHNICAL FIELD

The present invention relates to a method for producing xanthophyll efficiently.

BACKGROUND ART

Xanthophyll (e.g., astaxanthin, canthaxanthin, zeaxanthin, adonirubin, adonixanthin, cryptoxanthin, and the like), which is a carotenoid, has been used for various purposes. For example, astaxanthin, which is a carotenoid imparting a red color, is known to have a potent antioxidative effect. Thus, it is used as a pigment in food, a cosmetic, a health food product, a pharmaceutical, and the like. Some astaxanthins are chemically synthesized. Astaxanthins are also naturally occurring. The naturally occurring astaxanthins are extracted from, for example, Eucarida such as euphausiids and Pandalus borealis, from Phaffia yeast, and from algae. However, astaxanthin is not produced efficiently from Eucarida such as euphausiids or yeast because of their low astaxanthin content.

On the other hand, algae, e.g., Haematococcus, which are encysted as a result of a change in the external environment accumulate astaxanthin in the algal cells. Thus, production of astaxanthin from algae has been investigated.

For example, J. Fabregas et al., J. Biotech. Vol. 89, p 66, (2001) describes a method for producing astaxanthin by cultivating Haematococcus in two steps. According to this method, in the first step, vegetative cells of Haematococcus are obtained while exchanging 10 to 40% of a culture medium every day (i.e., fed-batch culture). In the second step, a batch culture is performed for an additional 15 days under irradiation with light to induce the vegetative cells to become dormant (i.e., undergo encystment) and accumulate astaxanthin within the cells.

R. T. Lorenz et al., TIBTECH, vol. 18 (April), p 160-167, (2000) describes a two-step culture method of Haematococcus for the purpose of producing astaxanthin commercially. According this method, in the first step Haematococcus is cultivated within a sealed bioreactor under light irradiation to obtain vegetative cells. In the second step, the vegetative cells are transferred to an outdoor culture pool containing a medium in which nitrogen and phosphorus are deficient, and then the vegetative cells are induced to become dormant (i.e., undergo encystment) and to accumulate astaxanthin within the cells, by cultivating the cells while increasing a culture temperature under the irradiation with light having the elevated intensity, or by cultivating the cells in the medium of the outdoor culture pool to which sodium chloride is added.

Japanese Laid-Open Patent Publication No. 2000-60532 describes a method in which, in the first step, Haematococcus is cultured within a sealed bioreactor under irradiation with light to obtain vegetative cells, and then, in the second step, the cells are shifted to the resting state in an outdoor culture pool to induce production and accumulation of astaxanthin, and the Haematococcus is collected before the growth of predaceous or parasitic organisms on Haematococcus.

However, with respect to the two-step methods described above, in the second step where cultivation is performed in an open or outdoor culture pool such as a raceway-type open-air culture tank, it is highly likely that various bacteria will grow in the medium. For this reason, it is necessary for the duration of the encystment period to be short, and the astaxanthin content of the encysted cells consequently is low. In order to increase the production efficiency of astaxanthin, it is necessary to prepare a large amount of vegetative cells.

Japanese Laid-Open Patent Publication No. 2004-129504 describes a method for producing astaxanthin by cultivating Haematococcus in the dark or without irradiation with light and under an aerobic condition, but this method has a problem of low astaxanthin productivity.

In view of the foregoing, there has been a demand for a method for producing astaxanthin efficiently from algae.

DISCLOSURE OF INVENTION

The present invention provides a method for producing a xanthophyll from a photosynthetic microalga, which includes inoculating a photosynthetic microalga containing a xanthophyll into a nutrient medium to grow the photosynthetic microalga; and encysting the grown microalga.

In an embodiment, the inoculated photosynthetic microalga containing the xanthophyll is an encysted photosynthetic microalga.

In another embodiment, the growth step and the encystment step are performed in a same culture tank.

Moreover, in another embodiment, the growth step and the encystment step are performed using a low nutrient medium.

In still another embodiment, the growth step and the encystment step are performed by batch culture.

In a still different embodiment, the growth step and the encystment step are performed independently using different media.

In another embodiment, the growth step and the encystment step are performed independently by batch culture.

Moreover, in an embodiment, the growth step and the encystment step are performed under irradiation with light.

In still another embodiment, the microalga is a green alga belonging to the genus Haematococcus.

Moreover, in another embodiment, the green alga is Haematococcus pluvialis.

In a still different embodiment, the xanthophyll is astaxanthin.

Moreover, the present invention provides a photosynthetic microalga having a zoospore containing a xanthophyll.

BEST MODE FOR CARRYING OUT THE INVENTION

Figure 1:
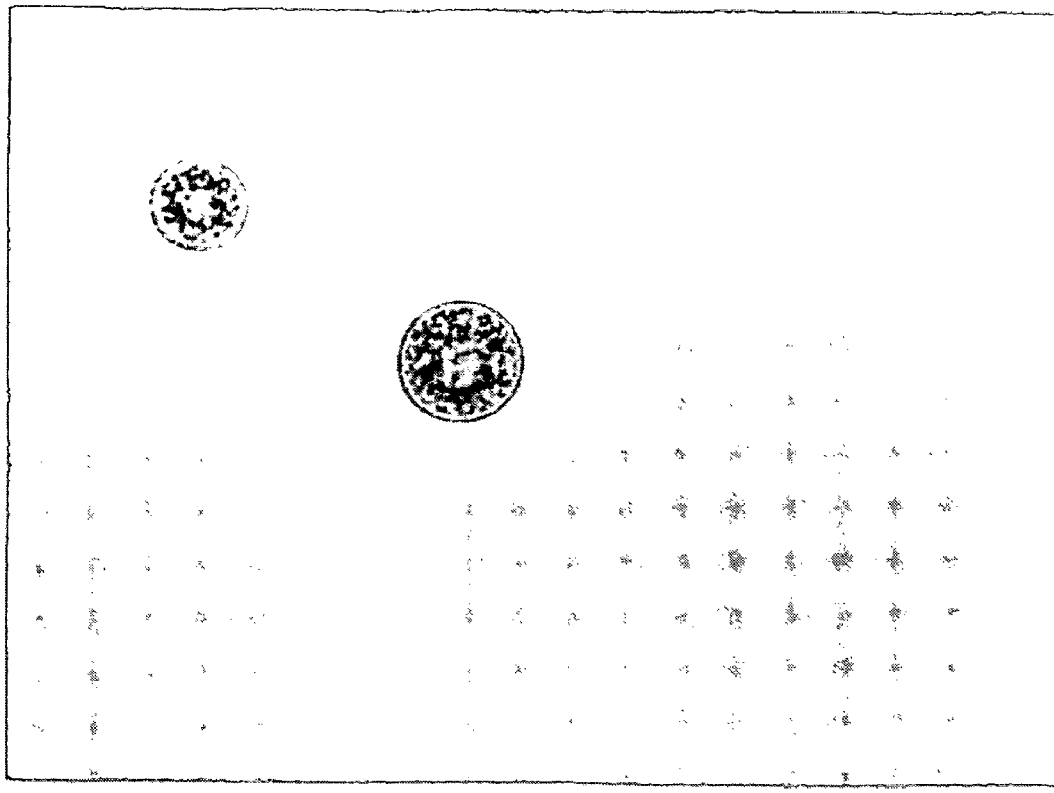
FIG. 1 shows a microphotograph of encysted cells of Haematococcus to be inoculated into a nutrient medium.

The method of the present invention is characterized in that photosynthetic microalgae containing xanthophyll, preferably encysted photosynthetic microalgae containing xanthophyll, are inoculated into a growth medium and grown, and then encysted. Hereinafter, the photosynthetic microalgae in this specification may be simply referred to as the "microalgae".

When the microalgae containing xanthophylls, preferably, the encysted microalgae that have accumulated a large amount of xanthophylls, are inoculated into a growth medium and grown, the encysted microalgae release zoospores containing xanthophyll. The zoospores become vegetative cells containing xanthophyll. The vegetative cells grow also by division into cells which contain xanthophyll. Therefore, the number of microalgae is increased faster than by simple cell division. Then, by further encysting the grown microalgae (i.e., the increased number of vegetative cells) containing xanthophyll, additional xanthophyll is produced and accumulated within the microalgal cells. Therefore, the microalgae encysted by the method of the present invention contain the newly produced xanthophyll in addition to the xanthophyll originally present, and thus have a higher xanthophyll content than in the case where vegetative cells of microalgae are simply encysted. Hereinafter, the present invention will be described in detail.

Photosynthetic Microalgae

There is no particular limitation on the photosynthetic microalgae used in the present invention, as long as the algae can photosynthesize and are capable of producing xanthophyll. From the point of view of xanthophyll production, green algae are preferably used.

As the green algae used in the present invention, for example, unicellular algae belonging to the genus *Haematococcus* are preferably used. Preferred examples of the algae belonging to the genus *Haematococcus* include *Haematococcus pluvialis* (*H. pluvialis*), *Haematococcus lacustris* (*H. lacustris*), *Haematococcus capensis* (*H. capensis*), *Haematococcus droebakensi* (*H. droebakensi*), and *Haematococcus zimbabwiensis* (*H. zimbabwiensis*). Examples of *Haematococcus pluvialis* (*H. pluvialis*) include the NIES144 strain deposited in the Independent Administrative Institution National Institute for Environmental Studies, the UTEX2505 strain deposited in the Culture Collection of Algae at the University of Texas at Austin, U.S. A., and the K0084 strain deposited in the Scandinavian Culture Center for Algae and Protozoa, Botanical Institute, at the University of Copenhagen, Denmark.

Examples of *Haematococcus lacustris* (*H. lacustris*) include the ATCC30402 and ATCC30453 strains deposited in ATCC, the IAM C-392, IAM C-393, IAM C-394, and IAM C-339 strains deposited in the Institute of Applied Microbiology, University of Tokyo, or the UTEX16 and UTEX294 strains.

Examples of *Haematococcus capensis* (*H. capensis*) include the UTEX LB1023 strain.

Examples of *Haematococcus droebakensi* (*H. droebakensi*) include the UTEX 55 strain.

Examples of *Haematococcus zimbabwiensis* (*H. zimbabwiensis*) include the UTEX LB1758 strain.

Among these, *Haematococcus pluvialis* is preferably used.

Encystment

In the present invention, a microalga as described above that contains xanthophyll is inoculated into a nutrient medium. The microalga containing xanthophyll may be a vegetative cell containing xanthophylls or an encysted microalga containing xanthophylls. The vegetative cell containing xanthophyll of a microalga means that the microalga was once encysted (i.e., in the dormant stage).

When microalgae are subjected to stresses from the environment, such as irradiation with light, nutrient deprivation, the presence of oxides, and the like, the microalgae accumulate xanthophyll and the like within the cells and become resting spores. The shift to this resting state is referred to as encystment. In this specification, encystment includes any state from when an alga enters the resting state and starts to accumulate xanthophyll to when the alga is completely encysted and becomes a resting spore. In order to increase the xanthophyll content, it is preferable to use microalgae in which encystment has progressed as far as possible and that have accumulated a large amount of xanthophyll.

Medium

There is no particular limitation on the medium used to cultivate the microalgae. Generally, a medium is used that contains nitrogen essential to growth, inorganic salts of trace metal (e.g., phosphorus, potassium, magnesium, iron), vitamins (e.g., thiamine), and the like. For example, media such as the VT medium, C medium, MC medium, MBM medium, and MDM medium (see Sorui Kenkyuho, ed. by Mitsuo Chihara and Kazutoshi Nishizawa, Kyoritsu Shuppan Co., Ltd. (1979)), the OHM medium (see J. Fabregas et al., ibid.), the BG-11 medium, and modifications thereof may be used.

These media may be selected depending on their purposes, such as the purpose of growth or the purpose of encystment. For example, for growth of the microalgae, a medium having a large amount of components serving as a nitrogen source is used (rich medium: containing at least 0.15 g/L expressed in terms of nitrogen). For encystment, a medium that is nearly free from components serving as nitrogen source is used (encystment medium: containing less than 0.02 g/L expressed in terms of nitrogen). Alternatively, a medium containing a nitrogen source at an intermediate concentration between these media may be used (low nutrient medium: containing at least 0.02 g/L and less than 0.15 g/L expressed in terms of nitrogen).

The nitrogen source concentration, phosphorus concentration, and other properties of the medium can be determined depending on the amount of microalgae to be inoculated. For example, in the case where the concentration of the microalgae (*Haematococcus*) at the start of cultivation is on the order of $10^5$, if a low nutrient medium is used, then the microalgae would grow to a certain extent, and the growth stops soon because the amount of the nitrogen source is too small. In such a case, the low nutrient medium is suitable in the case where growth and encystment are performed continuously in a single step (in a batch manner), as described below. Furthermore, by adjusting the N/P ratio (mole ratio) to 10 through 30, preferably 15 through 20, the microalgae can be encysted smoothly.

For a higher microalgae concentration at the start of cultivation, the cultivation can be performed using the rich medium as described above.

In this manner, the composition of the medium can be determined with consideration given to the various conditions.

It should be noted that the medium used in the present invention is nearly free from an organic carbon source such as acetic acid or glucose, so that contamination by bacteria hardly occurs even in long-term cultivation.

Culture Apparatus

As to the apparatus for cultivating the microalgae, there is no particular limitation as long as the apparatus is capable of supplying carbon dioxide and irradiating a cell suspension with light. For example, in the case of a small-scale culture a flat culture flask may be used. In the case of a large-scale culture, a plate culture tank that is constituted by a transparent plate made of glass, plastic, or the like, a culture tank equipped with an agitator and an irradiation apparatus, a tube-type culture tank, an airdome-type culture tank, a hollow cylinder-type culture tank, and the like may be used. A sealed container is preferably used.

Culture Conditions

There is no particular limitation regarding the culture conditions, and a temperature and a pH as generally employed for cultivation of microalgae are used. The microalgae are cultivated at, for example, 15 to 35° C and preferably 20 to 25° C. It is preferable that throughout the cultivation period the pH is maintained at 6 to 8. Carbon dioxide is supplied by bubbling a gas containing carbon dioxide at a concentration of 1 to 3 v/v % at 0.2 to 2 vvm, for example. When a plate culture tank is used, the cell suspension is stirred by supplying carbon dioxide, so that the microalgae are uniformly irradiated with light.

Irradiation with Light

When cultivating microalgae, usually irradiation with light is performed so that the photosynthetic photon flux density (PPFD) is about 100 μmol-photon/$m^2$s (hereinafter, this unit is abbreviated as μmol-p/$m^2$s). To increase the production of xanthophyll, 300 μmol-p/$m^2$s or more is preferable, and 500 μmol-p/$m^2$s or more is more preferable. By performing irradiation with light having a high PPFD as described above throughout the entire culture process from the start of cultivation to encystment, the production of astaxanthin is increased. The PPFD is a photon flux density measured by using a LICOR-190SA flat-surface photon sensor (LICOR Inc., Lincoln, USA), and is a value obtained with the sensor placed in the center of the culture apparatus without a medium under irradiation with light. In the case of an apparatus constituted by a transparent plate such as glass or acrylic resin, a light source may be positioned by measuring the PPFD passing through the transparent plate and determining the illuminance of light or the distance of the light source required for obtaining a predetermined PPFD.

Culture Method

Microalgae is cultivated under irradiation with light by appropriately selecting and combining the above-described media, culture apparatuses, culture conditions, and the like. There are two culture methods. One method is a single-step culture in which encysted microalgae inoculated into a nutrient medium are grown and encysted continuously in the same medium. The other method is a two-step culture in which the medium for growing encysted microalgae and the medium for encysting the microalgae are different from each other, and growth and encystment are performed separately.

The single-step culture is a method of cultivating continuously the encysted microalgae without exchanging the medium during the period from inoculation to the end of the cultivation. That is, it is a method in which growth and encystment of the microalgae are performed with a predetermined medium in the same culture tank. This single-step culture is not suitable for continuous culture and is preferably performed in a batch manner. In this single-step culture, once the microalgae has grown, the microalgae are shifted to an encysted state smoothly under at least one of the following stresses: nutrient starvation stress due to consumption of nutrient components in the medium, stress due to irradiation with light, thermal stress due to a high temperature, and stress due to addition of sodium chloride.

When a microalga containing xanthophyll, preferably encysted microalga, is inoculated into the nutrient medium, the microalga releases $2^n$ (n=1 to 4) zoospores containing xanthophyll. The zoospores become vegetative cells containing xanthophyll, so that the number of vegetative cells containing xanthophyll increases (i.e., the microalga grows). Furthermore, the vegetative cells grow by cell division. By encysting vegetative cells containing xanthophyll, xanthophyll is newly accumulated in addition to the xanthophyll originally contained in the vegetative cells, and thus the xanthophyll content is increased.

It is believed that when the vegetative cells continue to grow, the xanthophyll concentration in the cells eventually decreases, and therefore it is preferable to stop growth at a point where xanthophyll remains in the cells.

In order to stop growth of the microalgae at the point when the vegetative cells have grown to a certain extent, it is preferable that the medium be designed so as to be nutrient-starved at that time. For this purpose, in the single-step culture, a medium having a low nitrogen source concentration, for example, the low nutrient medium described above, is preferably used. When a large amount of encysted cells is to be inoculated, a medium having a high nitrogen source concentration, for example, the rich medium described above, may be used.

It should be noted that when the microalgae do not grow sufficiently in the low nutrient medium, a rich medium or a low nutrient medium can be supplemented so as to grow the microalgae to a desired extent.

Moreover, in the case where the low nutrient medium is used, if the N/P ratio (mole ratio) is adjusted to be between 10 and 30, then the microalgae can be encysted smoothly after growth.

The single-step culture has advantages such as that process control can be performed easily, that microalgae containing xanthophyll at high concentration can be obtained easily, that contamination can be prevented because transfer of the microalgae to another culture tank is not necessary, and that the method can be performed with a single culture tank.

The two-step culture is a method of growing encysted microalgae and then transferring the microalgae to an encystment medium for encystment. That is, the two-step culture includes a first step in which the encysted microalgae are first inoculated into a rich medium or a low nutrient medium, preferably into a rich medium, to grow the microalgae, and a second step in which the microalgae are collected and transferred to an encystment medium that is nearly free from the nitrogen source, and then encysted.

It is necessary to finish growth of the microalgae in the first step while xanthophyll remains in the vegetative cells, so that cultivation in the nutrient medium is performed for a short period of time. When the cultivation is performed using a rich medium at the start of the cultivation, the growth rate of the vegetative cells is higher than the growth rate when a low nutrient medium is used, and therefore it is preferable to use a rich medium. After growth, the microalgae are collected and transferred to the encystment medium, and encysted in the second step.

The first step and the second step may be performed independently in a batch manner in separate culture tanks. It is also possible to wash and collect the grown microalgae at the end of the first step, place the microalgae back in the same culture tank, and then perform the second step.

With the two-step culture, microalgae having a high xanthophyll content can also be obtained. The two-step culture has an advantage in that the growth step can be finished in a shorter period of time than with the single-step culture method; however, the operation of transferring the grown microalgae is required in the two-step process.

It is also possible to use a portion of the obtained encysted microalgae for collecting xanthophyll and a portion of the remainder for another inoculation into a nutrient medium.

Collection of Xanthophyll

Since xanthophyll is accumulated within the microalgae by encystment of the microalgae, xanthophyll can be collected using a routine procedure after collecting the algae. For example, a method of mechanically destroying the microalgae and then extracting the xanthophyll with an organic solvent can be employed.

EXAMPLES

Hereinafter, the present invention will be described by way of examples, but the present invention is not limited to these examples.

In these examples, measurements of chlorophyll, xanthophyll, and dry algae were carried out as follows.

Measurement of Chlorophyll

First, 5 ml of a cell suspension were collected and centrifuged (3500 rpm, 5 minutes) to collect the microalgae. The microalgae were dispersed by vortexing, and then, 5 ml of dimethyl sulfoxide (DMSO) were added thereto and dispersed, and the mixture was allowed to stand with shielding from light for 30 minutes. Subsequently, the mixture was heated in a thermostat water bath at 70° C for 10 minutes, and centrifuged to collect a DMSO fraction. If the precipitate is colored, then 5 ml of DMSO are further added thereto and the above-described operation is repeated. This operation is repeated until the color of the cells becomes white. The collected DMSO fractions are combined, and the absorbance at 672 nm is measured using a spectrophotometer (Hitachi spectrophotometer U-3210). The chlorophyll concentration can be calculated using the following equation:

Chlorophyll concentration (μg/ml)=13.9×dilution factor×absorbance

Measurement of Xanthophyll

First, 5 ml of the cell suspension are collected and centrifuged (3500 rpm, 5 minutes) to collect the microalgae. The microalgae are dispersed by vortexing, and 5 ml of 30 (v/v)% aqueous methanol containing 5 wt % of KOH are added thereto, and then, the microalgae are vortexed and dispersed, and the mixture is treated in a thermostat water bath at 70° C for 10 minutes. By this treatment, chlorophyll is decomposed. The mixture is centrifuged (3500 rpm, 5 minutes) again to recover a precipitate. After vortexing, residual alkali is neutralized using an acid (e.g., acetic acid). After neutralization, 5 ml of DMSO are added thereto, and the mixture is allowed to stand with shielding from light for 20 minutes and further treated at 70° C for 10 minutes. By centrifuging (3500 rpm, 5 minutes), a supernatant is collected. If the precipitate is colored, then 5 ml of DMSO are further added thereto and the above-described operation is repeated. This operation is repeated until the color of the cells becomes white. The collected DMSO fractions are combined, and the absorbance at 492 nm is measured. The xanthophyll concentration can be calculated using the following equation:

Xanthophyll concentration (μg/ml)=4.5×dilution factor×absorbance

Most of the xanthophyll produced by *Haematococcus pluvialis* in the examples below is astaxanthin. Measurement of astaxanthin is performed in the same manner as the above-described method for measuring xanthophylls.

Dry Weight of Microalgae

First, a predetermined amount of the cell suspension was collected and filtered on a GC50 glass fiber filter (made by ADVANTEC TOYO Kaisha, Ltd.) under reduced pressure, and then washed twice with 5 ml of aqueous solution of hydrochloric acid having a pH of 4 to dissolve inorganic salts. Thereafter, the microalgae together with the filter were dried in a thermostatic drier at 105° C for 3 hours, and cooled in a vacuum desiccator for one hour to room temperature, and then the dry weight was measured. The weight of the GC50 glass fiber filter was preliminarily measured by drying the filter in the thermostatic drier at 105° C for one hour.

Example 1

Preculture: Preparation of Encysted Cells for Growth

*Haematococcus pluvialis* K0084 strain (hereinafter, simply referred to as the "K0084 strain") that produces astaxanthin, which is a xanthophyll, was used. First, 1 L of a MBG-11 medium containing the components shown in Table 1 below was placed in a 1.5 L sealed flat culture flask having a light path of 25 mm, and the K0084 strain was inoculated into the medium so that the initial concentration was 0.6 g/L. The N/P ratio of the MBG-11 medium was 20.

TABLE 1

| Components of MBG-11 medium | g/L |
|---|---|
| $KNO_3$ | 0.41 |
| $K_2HPO_4$ | 0.04 |
| $MgSO_4 \cdot 7H_2O$ | 0.075 |
| $CaCl_2 \cdot 2H_2O$ | 0.036 |
| Citric acid (anhydrous) | 0.006 |
| Ammonium iron (III) citrate | 0.006 |
| $EDTA \cdot 2Na$ | 0.001 |
| $Na_2CO_3$ | 0.02 |
| $CuSO_4 \cdot 5H_2O$ | 0.00286 |
| $H_3BO_4$ | 0.00181 |
| $MnCl_2 \cdot 4H_2O$ | 0.00022 |
| $ZnSO_4 \cdot 7H_2O$ | 0.00008 |
| $Na_2MoO_4$ | 0.000021 |
| $Co(NO_3)_2 \cdot 6H_2O$ | 0.000000494 |

The K0084 strain was cultivated for 5 days under the light irradiation conditions described below while bubbling a gas containing 3 vol % of $CO_2$ at a rate of 600 ml/minute (i.e., at 0.6 vvm) and adjusting the culture temperature to 25° C and the pH to between 6 and 8.

For irradiation of light, a white fluorescent lamp (made by National, FL40SSW/37) was used as the light source. The intensity of light irradiation was adjusted so that the PPFD in the light receiving direction of the culture tank measured using the LICOR-190SA flat-surface photon sensor was 100 μmol-p/m²s.

The K0084 strain after the cultivation was changed in color from green to brown or blackish brown, and was confirmed to have been encysted. This encysted K0084 strain contained 1.2% by weight of astaxanthin per dry weight. A microphotograph of the encysted cells obtained by this method and used for inoculation into a nutrient medium is shown in FIG. 1.

Main Culture: Growth of the Encysted Cells and Encystment of the Grown Cells

Using the same flat culture flask as described above, the encysted K0084 strain was inoculated into the same medium (MBG-11 medium) so that the initial concentration was 0.6 g/L, and was cultivated under the same culture conditions as described above.

Figure 3:
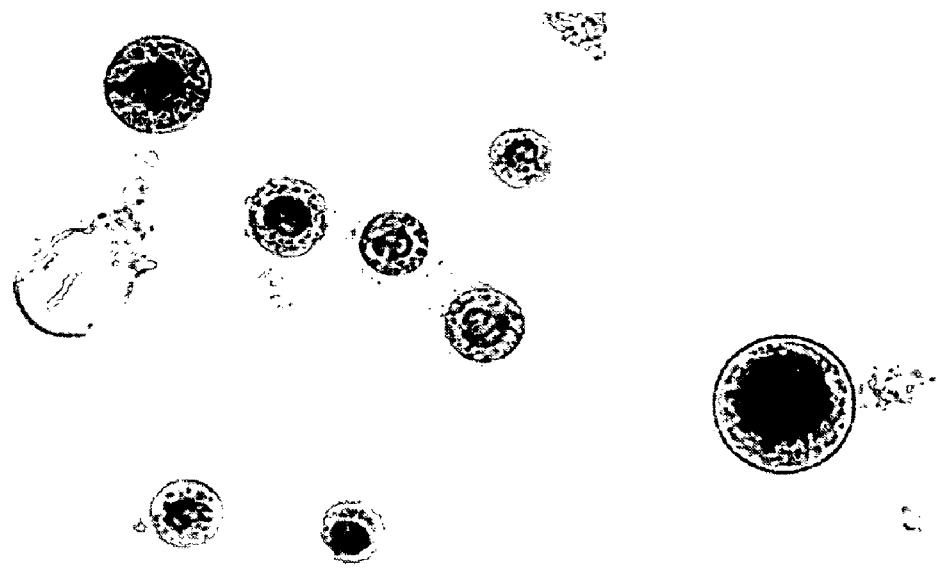
FIG. 3 shows microphotographs of those Haematococcus cells at the 200th hour after the start of the culturing.
Figure 4:
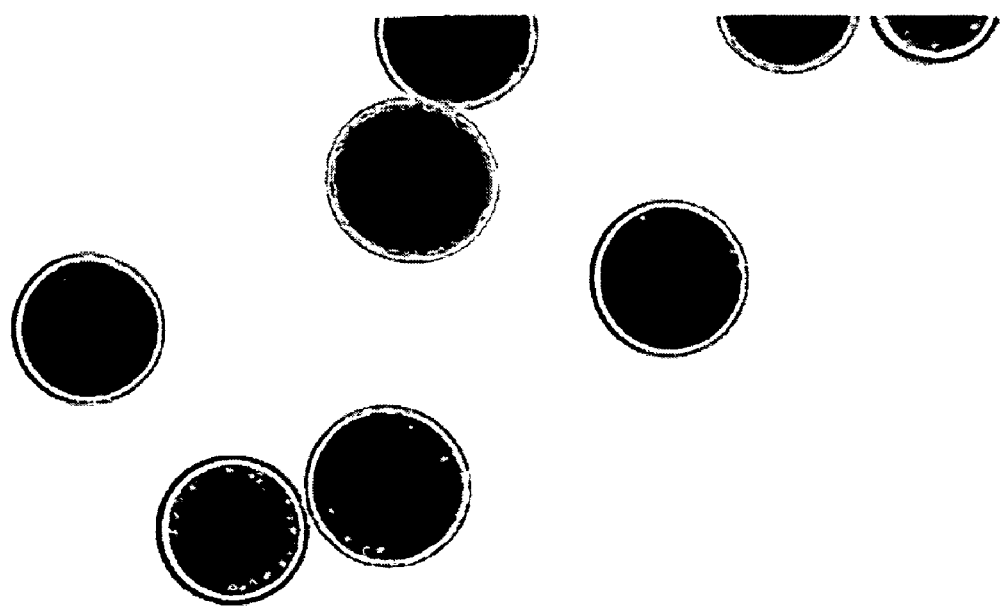
FIG. 4 shows a microphotograph of those Haematococcus cells at the 350th hour after the start of the culturing.
Figure 5:
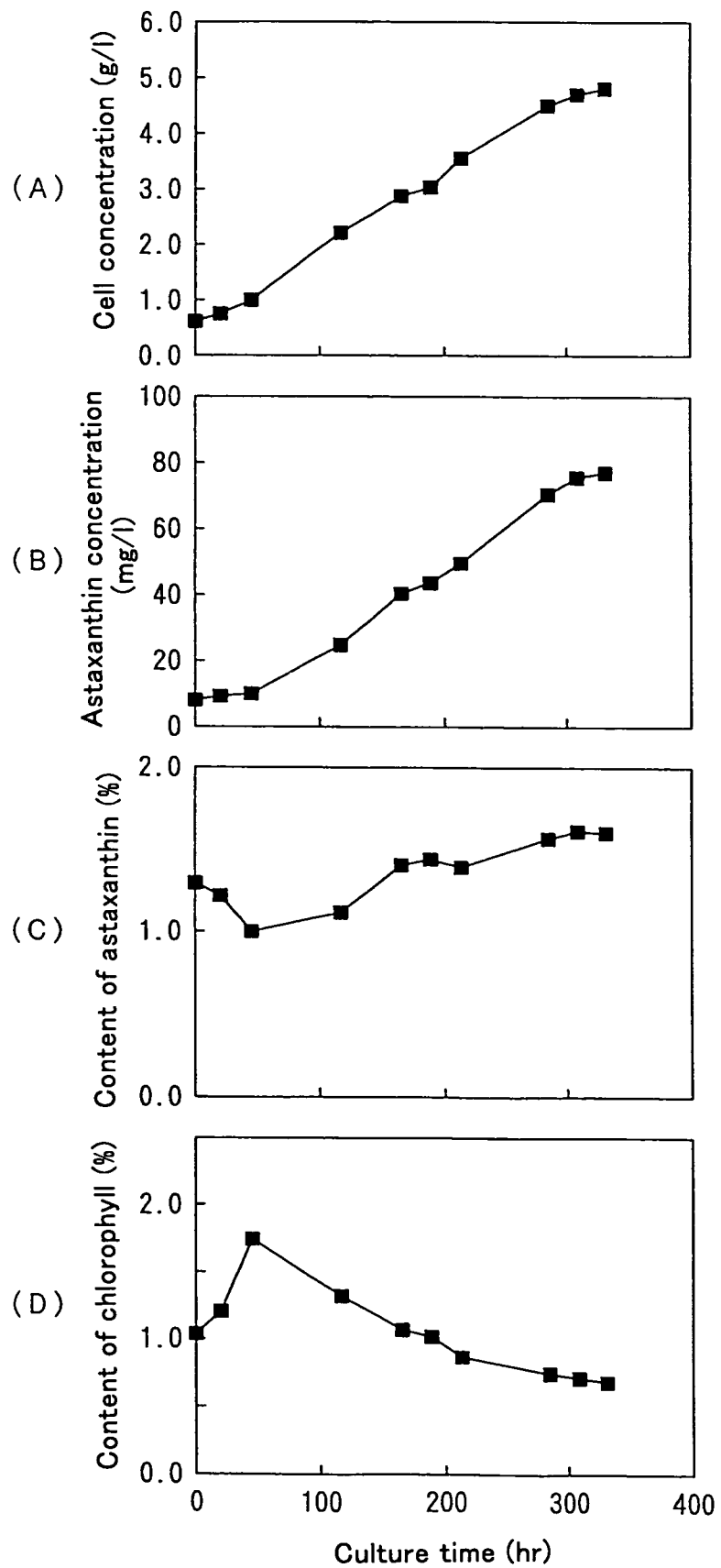
FIG. 5 presents graphs showing the growth of algae and the change in astaxanthin content over time in a single-step culture method according to the present invention.

The cultivation process will be described with reference to FIGS. 1 to 4 and FIG. 5. At the start of the cultivation, the K0084 strain was dark brown as shown in FIG. 1, and the astaxanthin content per dry alga weight was about 1.2% as described above. After the start of the cultivation, as shown in FIGS. 5(c) and 5(d), the astaxanthin content per dry alga weight decreases for a while, whereas the chlorophyll content per dry alga weight increases. Then, from about the 50th hour, these are reversed. That is, after the 50th hour, the astaxanthin content per dry alga weight increases, and the chlorophyll content per dry alga weight decreases. It is apparent that the 50th hour is a time when growth stops and shifts to encystment.

Figure 2:
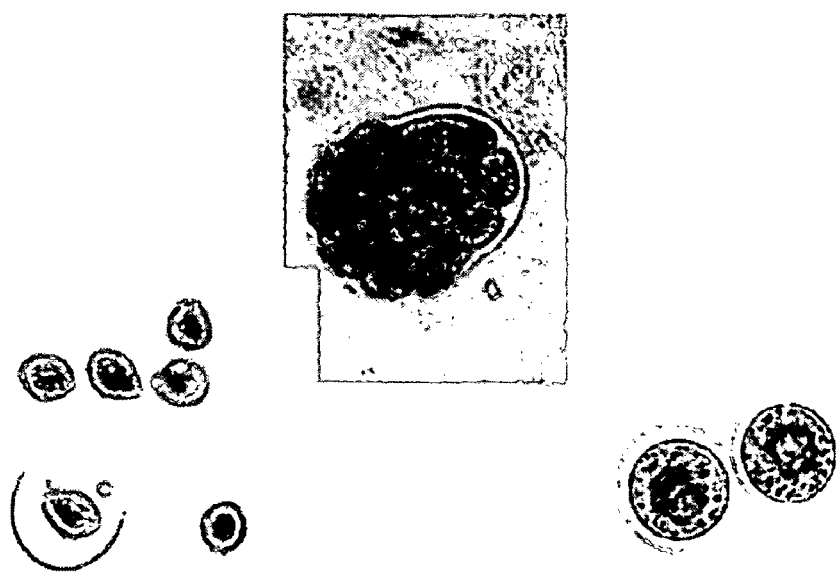
FIG. 2 shows microphotographs of those Haematococcus cells at the 50th hour after the start of culturing.

Microphotographs of the cells at the 50th hour are shown in FIG. 2. As can be seen from FIG. 2, the encysted *Haematococcus* cells contained zoospores tinged with red. It was also found that the zoospores were released and changed into vegetative cells. That is, a green layer that indicated an accumulation of chlorophyll was found inside the cell wall generated from the zoospores.

When the cultivation was further continued, the astaxanthin content per dry alga weight increased gradually, and chlorophyll decreased. Microphotographs of the cells at the 200th hour after the start of the cultivation are shown in FIG. 3, and a microphotograph at the 350th hour is shown in FIG. 4. For the cells in FIG. 3, which are after 200 hours, it was found that the size of the cells had increased and also that dark brown astaxanthin had accumulated inside the green layer (chlorophyll layer) which was formed inside the cells. At the 350th hour, it was found that the size of the cells had further increased and a red material occupied the inside of the cell wall. The process described above was very consistent with the increase over time in the cell concentration shown in FIG. 5(A) and the increase over time in the astaxanthin concentration in cell suspension shown in FIG. 5(B). The results in cultivation at the 350th hour are shown in Table 2.

Reference Example 1

Cultivation was performed for 350 hours in the same manner as in Example 1, except that unencysted vegetative cells of the K0084 strain were inoculated into a MBG-11 medium. The results are shown in Table 2.

TABLE 2

| | Amount of xanthophyll | |
|---|---|---|
| | Per dry alga body (wt/wt %) | Concentration in cell suspension (mg/l) |
| Ex. 1 | 1.8 | 80 |
| Ref. Ex. 1 | 0.9 | 42 |

As can be seen from Table 2, it is found that by inoculating and growing the encysted microalgae (*Haematococcus*) and then encysting the microalgae, the concentration in cell suspension and the content per dry alga weight of astaxanthin were increased when compared to the case where vegetative cells were inoculated and grown.

Example 2

The two-step cultivation in which encysted microalgae were grown in a nutrient medium and then transferred to an encystment medium was examined.

The media shown in Table 3 below were prepared. The BG-11 medium in Table 3 is a rich medium containing 1.5 g/L of sodium nitrate instead of 0.41 g of potassium nitrate ($KNO_3$) as in the MBG-11 medium used in the single-step cultivation of Example 1. On the other hand, the NBG-11 medium is an encystment medium that does not contain a nitrogen source such as sodium nitrate or potassium nitrate, nor does it contain phosphorus.

TABLE 3

| Medium name Components | BG-11 g/L | NBG-11 g/L |
|---|---|---|
| $NaNO_3$ | 1.5 | 0 |
| $K_2HPO_4$ | 0.04 | 0 |
| $MgSO_4 \cdot 7H_2O$ | 0.075 | 0.075 |
| $CaCl_2 \cdot 2H_2O$ | 0.036 | 0.036 |
| Citric acid (anhydrous) | 0.006 | 0.006 |
| Ammonium iron (III) citrate | 0.006 | 0.006 |
| EDTA·2Na | 0.001 | 0.001 |
| $Na_2CO_3$ | 0.02 | 0.02 |
| $CuSO_4 \cdot 5H_2O$ | 0.00286 | 0.00286 |
| $H_3BO_4$ | 0.00181 | 0.00181 |
| $MnCl_2 \cdot 4H_2O$ | 0.00022 | 0.00022 |
| $ZnSO_4 \cdot 7H_2O$ | 0.00008 | 0.00008 |
| $Na_2MoO_4$ | 0.000021 | 0.000021 |
| $Co(NO_3)_2 \cdot 6H_2O$ | 0.000000494 | 0.000000494 |

The K0084 strain, that was cultivated under the same conditions as in Example 1 and encysted, was collected, washed, and inoculated into 1 L of the BG-11 medium in Table 3 so that the initial concentration was 0.6 g/L. Then, cultivation was started under the same culture conditions as in Example 1, except that the intensity of light irradiation was adjusted so that the PPFD was 300 μmol-p/m$^2$s. The K0084 strain was collected after 120 hours (5 days) and inoculated into the NBG-11 medium (medium for encystment), and the cultivation was further continued using the same flat culture flask under the same culture conditions. The results after cultivation for 400 hours are shown in Table 4.

Example 3

Encysted cells were inoculated and cultivated, using a MBG-11 medium, in a single step under the same culture conditions as in Example 1, except that the conditions of light irradiation were adjusted so that the PPFD was 300 μmol-p/m$^2$s. The results after cultivation for 400 hours are shown in Table 4.

Reference Example 2

The two-step cultivation was performed in the same manner as in Example 2, except that vegetative cells were inoculated into a BG-11 medium. The results after cultivation for 400 hours are shown in Table 4.

TABLE 4

| | | | | Amount of xanthophyll | |
|---|---|---|---|---|---|
| | Culture method | Amount of dry alga body (g/L) | Content[*1] (wt/wt %) | | Concentration in cell suspension (mg/l) |
| Ex. 2 | Two-step culture | 8.0 | 2.9 | | 240 |
| Ex. 3 | Single-step culture | 7.8 | 3.5 | | 270 |
| Ref. Ex. 2 | Two-step culture | 7.7 | 1.9 | | 142 |

[*1]Amount of xanthophyll per dry alga body

These results indicate that by growing encysted microalgae containing astaxanthin or growing microalgae containing astaxanthin and then encysting the microalgae, microalgae having a high astaxanthin content can be obtained. Also, these results indicate that both the single-step culture method and the two-step culture method are useful methods for obtaining microalgae having a high astaxanthin content.

INDUSTRIAL APPLICABILITY

According to the present invention, by inoculating and growing microalgae containing xanthophyll, for example, encysted microalgae, and then encysting the microalgae, encysted microalgae containing xanthophyll at a high concentration can be obtained. Moreover, a part of the obtained encysted microalgae is used for next cultivation. Thus, the present invention is industrially useful as a method for culturing and producing xanthophyll effectively from microalgae.

The invention claimed is:

1. A method for producing a xanthophyll from a photosynthetic microalga, comprising:
   a growth step wherein an encysted photosynthetic microalga containing xanthophyll is inoculated into a nutrient medium and grown; and
   an encystment step wherein the microalga obtained in the growth step is cultivated under an encystment condition,
   wherein the growth step and the encystment step are performed using a low nutrient medium, wherein the concentration of nitrogen source in the low nutrient medium is at least 0.02 g/L and less than 0.15 g/L expressed in terms of nitrogen.

2. The method of claim 1, wherein the growth step and the encystment step are performed in a same culture tank.

3. The method of claim 1, wherein the growth step and the encystment step are performed by batch culture.

4. The method of claim 1, wherein the nutrient medium for the growth step and the nutrient medium for the encystment step are different from each other.

5. The method of claim 4, wherein the growth step and the encystment step are performed independently by batch culture.

6. The method of claim 1, wherein the growth step and the encystment step are performed under light irradiation.

7. The method of claim 1, wherein the microalga is a green alga belonging to the genus *Haematococcus*.

8. The method of claim 1, wherein the green alga is *Haematococcus pluvialis*.

9. The method of claim 1, wherein the xanthophyll is astaxanthin.

* * * * *